United States Patent
Sathyanarayana (10) Patent No.: US 7,306,561 B2
(45) Date of Patent: Dec. 11, 2007

(54) SYSTEMS AND METHODS FOR AUTOMATIC TIME-GAIN COMPENSATION IN AN ULTRASOUND IMAGING SYSTEM

(75) Inventor: Shashidhar Sathyanarayana, Union City, CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 64 days.

(21) Appl. No.: 10/933,994

(22) Filed: Sep. 2, 2004

(65) Prior Publication Data

US 2006/0058657 A1    Mar. 16, 2006

(51) Int. Cl.
*A61B 8/00* (2006.01)
*A61B 8/12* (2006.01)
*G01N 29/00* (2006.01)

(52) U.S. Cl. .................. 600/443; 600/667; 73/631
(58) Field of Classification Search ............... 600/437, 600/443–448, 462–471; 73/631
See application file for complete search history.

(56) References Cited

U.S. PATENT DOCUMENTS

| | | | |
|---|---|---|---|
| 4,043,181 A | 8/1977 | Nigam | |
| 4,057,049 A | 11/1977 | Hill | |
| 4,550,607 A | 11/1985 | Maslak et al. | |
| 4,662,380 A | 5/1987 | Riley | |
| 5,125,410 A | 6/1992 | Misono et al. | |
| 5,257,624 A | 11/1993 | Fraser et al. | |
| 5,375,470 A | 12/1994 | Matsushima et al. | |
| 5,477,858 A | 12/1995 | Norris et al. | |
| 5,485,845 A * | 1/1996 | Verdonk et al. | 600/463 |
| 5,501,221 A | 3/1996 | Foster et al. | |
| 5,579,768 A * | 12/1996 | Klesenski | 600/442 |
| 5,640,961 A * | 6/1997 | Verdonk | 600/459 |
| 6,050,947 A | 4/2000 | Rhyne et al. | |
| 6,102,859 A * | 8/2000 | Mo | 600/443 |
| 6,120,446 A | 9/2000 | Ji et al. | |
| 6,142,940 A | 11/2000 | Lathbury et al. | |
| 6,159,153 A | 12/2000 | Dubberstein et al. | |
| 6,263,094 B1 | 7/2001 | Rosich et al. | |
| 6,579,238 B1 * | 6/2003 | Simopoulos et al. | 600/443 |
| 6,592,520 B1 * | 7/2003 | Peszynski et al. | 600/437 |
| 6,621,341 B1 | 9/2003 | Shifrin | |
| 6,743,174 B2 | 6/2004 | Ng et al. | |

(Continued)

FOREIGN PATENT DOCUMENTS

DE    4439796 C1    4/1996

(Continued)

*Primary Examiner*—Francis J. Jaworski
(74) *Attorney, Agent, or Firm*—Orrick Herrington & Sutcliffe LLP (57) ABSTRACT

The systems and methods described herein provide for automatic time-gain compensation of an ultrasound image with an image processing algorithm. A method of automatic time-gain compensation is provided where ultrasound image data is obtained comprising a plurality of echogenic data sets, a plurality of time-gain compensation functions are determined for the plurality of echogenic data sets, wherein each time-gain compensation function is determined from a separate echogenic data set and the time-gain compensation functions are applied to the plurality of echogenic data sets automatically without user intervention. Also provided is an ultrasound imaging system having an ultrasound imaging device configured to collect ultrasound image data and an image processing system configured to automatically time-gain compensate the collected image data.

24 Claims, 5 Drawing Sheets

U.S. PATENT DOCUMENTS

| | | |
|---|---|---|
| 2002/0087218 A1 | 7/2002 | Amemiya |
| 2003/0023393 A1 | 1/2003 | Oravecz |
| 2004/0002435 A1 | 1/2004 | Petersen et al. |
| 2004/0006273 A1 | 1/2004 | Kim et al. |
| 2004/0039286 A1 | 2/2004 | Kuban et al. |

FOREIGN PATENT DOCUMENTS

| | | |
|---|---|---|
| EP | 0003595 A | 8/1979 |
| WO | WO 01/82787 A2 | 11/2001 |
| WO | WO 03/083506 A1 | 10/2003 |

* cited by examiner

SYSTEMS AND METHODS FOR AUTOMATIC TIME-GAIN COMPENSATION IN AN ULTRASOUND IMAGING SYSTEM

FIELD OF THE INVENTION

The systems and methods relate generally to automatic time-gain compensation in the ultrasound imaging of a living being.

BACKGROUND INFORMATION

In ultrasound imaging, the internal body is imaged by first transmitting an ultrasound wave towards an area of interest and then receiving the reflections generated as the wave passes through the internal body tissue at various depths. The ultrasound wave is typically generated and received using one or more ultrasound transducers. Imaging hardware and/or software within an imaging system stores the set of reflections, or echoes, received from each ultrasound transmission as an echogenic data sets, also referred to as an echo record or scan-line. This echogenic data set is used to generate a visual image displaying body features at various depths, the existence of which is correlated to time echoes are received and the echo's relative amplitude. Echoes received earlier in time are displayed as shallow features located close to the transducer, while echoes received later in time are shown as deeper features.

Certain portions in the body, such as bone, have a higher echogenicity than other, softer portions such as muscle or blood. These highly echogenic portions reflect more of the incident ultrasonic wave and create echoes having a greater amplitude than portions having a relatively low echogenicity. In the image, each echo is assigned a brightness value based on the level of the echo amplitude. This provides the viewer with additional information regarding the composition of the portions of the body located within the region of interest.

However, the ultrasound wave diminishes in amplitude, or attenuates, as it travels through the body tissue. As a result, the echoes generated by portions of the body located close to the transducer are relatively stronger than those generated at a greater distance from the transducer. If left uncorrected, the resulting image can incorrectly represent the objective echogenicity of the various body structures. An uncorrected image might even exhibit excessive brightness in the region close to the transducer, while leaving the rest of the image dark.

Figure 1A:
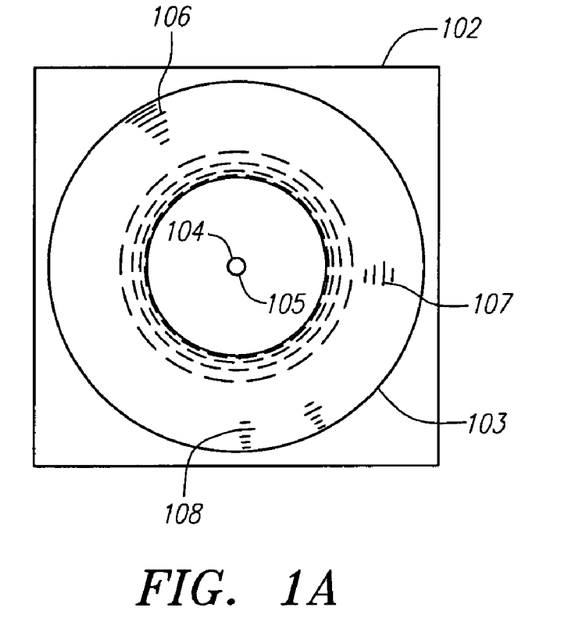
FIGS. 1A-B depict example conventional ultrasound images of a blood vessel.

An example of an uncorrected ultrasound image 102 is depicted in FIG. 1A. This exemplary image 102 is representative of one obtained with an intravascular imaging device, such as a catheter and the like, placed within a blood vessel. Shown within the field 103 of image 102 is the catheter outer wall 104, a blood vessel wall 105 and various tissue features 106-108 in and around the vessel wall 105. Here, it can be seen that the vessel wall 105 is relatively brighter than the surrounding tissue features 106-108 due to the attenuation of the transmitted ultrasound signal.

Figure 1B:
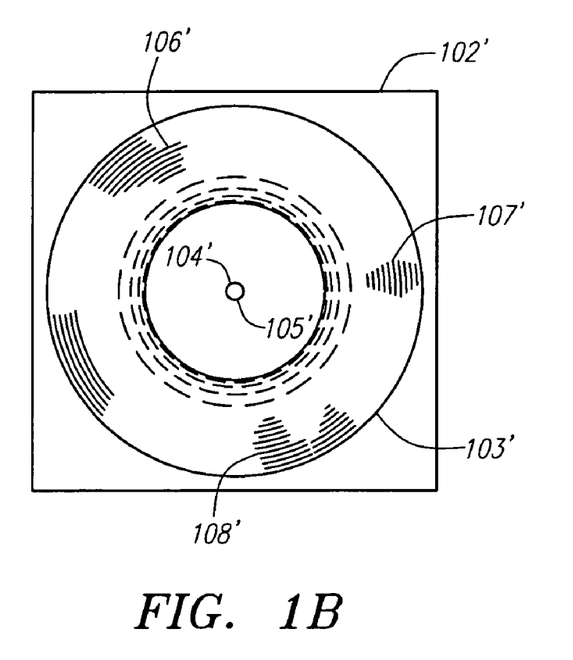

To compensate for this, conventional ultrasound imaging systems employ special hardware and/or software in the signal path to multiply the amplitude of each incoming echo signal by a time-varying amplification factor that amplifies echoes to a greater degree the later in time that they are received. The operation of applying this time-varying amplification is often referred to as "Time Gain Compensation" or TGC. A manual TGC input interface (consisting of a number of sliding controls, one for each range of depths) is typically provided in ultrasound systems to allow the user to adjust the time-varying amplification to achieve a desired result. An example of a time-gain compensated ultrasound image 102' is depicted in FIG. 1B. Here, it can be seen that the vessel wall 105 and the surrounding tissue features 106-108 all have comparable brightness levels as a result of the TGC.

Recently, an automatic TGC technique was proposed in U.S. Pat. No. 6,743,174 entitled "Ultrasonic diagnostic imaging system with automatically controlled contrast and brightness," which is fully incorporated herein by reference. This technique, targeted for use with an external ultrasound device, allows a user to time-gain compensate an image without having to manually adjust the gain levels for each depth. However, this technique still requires user-initiated input to initialize the TGC settings and therefore is not fully automatic. Also, this technique relies on predetermined gain levels stored in memory to serve as baseline gain values. Only after these predetermined gain values are applied does the technique attempt to determine what additional correction is necessary. Furthermore, this technique can only determine one gain value for each depth in the image and is incapable of determining a gain value for each depth along the individual scan-lines within the image.

Accordingly, improved automatic TCG systems and methods are needed that can overcome the shortcomings of conventional techniques while at the same time providing greater performance.

SUMMARY

The systems and methods provided herein allow for automatic TGC of an ultrasound image with an image processing algorithm. In an example method of automatic TGC, ultrasound image data is obtained, wherein the image data comprises a plurality of echogenic data sets. A plurality of TGC functions are determined for the plurality of echogenic data sets, wherein each TGC function is determined from a separate echogenic data set. The TGC functions are applied to the plurality of echogenic data sets automatically without user intervention.

Numerous TGC functions can be implemented with the systems and methods described herein. In one example, determining the TGC functions includes locally averaging the echogenic data sets, optionally applying an overflow suppression factor to the echogenic data sets, optionally applying a noise suppression factor to the echogenic data sets and determining the reciprocals of the low-pass filtered and optionally overflow and noise suppressed echogenic data sets. In this example, applying the TGC functions can include multiplying the original echogenic data sets by the reciprocal records.

One exemplary embodiment of an ultrasound imaging system configured to automatically time-gain compensate an ultrasound image includes an ultrasound imaging device configured to collect ultrasound image data and an image processing system communicatively coupled with the ultrasound imaging device. The image processing system can be configured to process an imaging signal received from the ultrasound imaging device into a plurality of echogenic data sets, determine a plurality of TGC functions for the plurality of echogenic data sets, wherein each TGC function is determined from a separate echogenic data set and apply the TGC functions to the plurality of echogenic data sets automatically without user intervention.

In another exemplary embodiment, the image processing system is configured to locally average the echogenic data sets and perform a magnitude adjustment, in part by determining the reciprocal of the averaged data sets. The image processing system can also be configured to optionally apply an overflow suppressing offset to the locally averaged data sets prior to determining the reciprocal and optionally apply a noise suppression factor to the locally averaged data sets prior to determining the reciprocal. Also, the image processing system can be configured to multiply the reciprocal data sets by the original echogenic data sets.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims. It is also intended that the invention is not limited to require the details of the example embodiments.

BRIEF DESCRIPTION OF THE FIGURES

The details of the invention, including fabrication, structure and operation, may be gleaned in part by study of the accompanying figures, in which like reference numerals refer to like segments.

DETAILED DESCRIPTION

The systems and methods described herein provide improved automatic TGC for ultrasound imaging. More specifically, the systems and methods allow TGC of an ultrasound image automatically without user input. TGC can be applied individually to each collected echogenic data set or to groups of related echogenic data sets. Similar to a scan-line, each echogenic data set preferably includes data collected in response to ultrasound transmission in one direction, or at one position of an ultrasound imaging device. The capability for automatic TGC of each individual echogenic data set within an image can result in a more accurately compensated overall image. Also, automatic TGC can be applied to the echogenic data sets as they are obtained, allowing the user to view the time-gain compensated ultrasound image in real-time.

Figure 2:
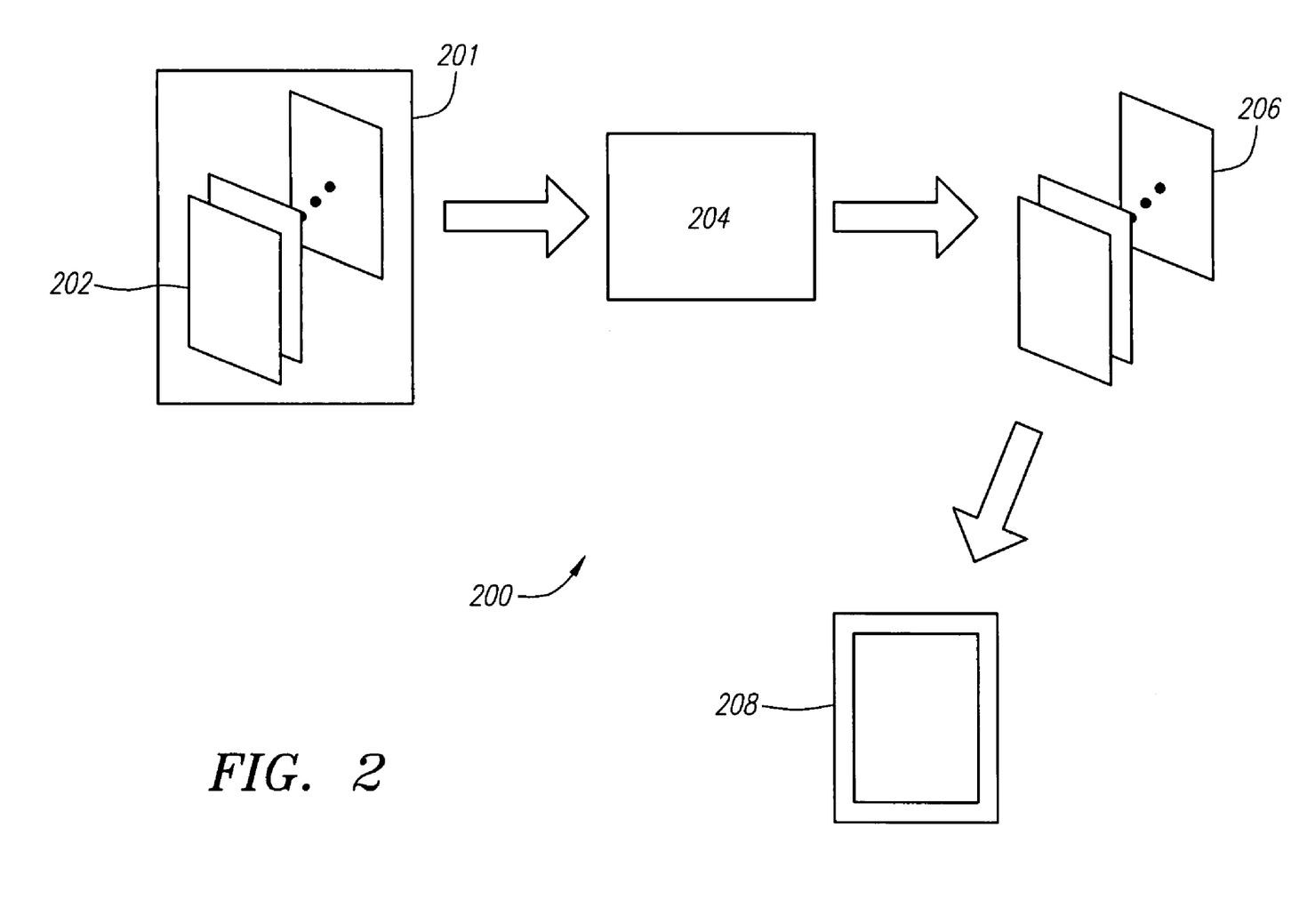
FIG. 2 depicts a block diagram of an exemplary method 200 of automatically time-gain compensating an ultrasound image.

FIG. 2 depicts a block diagram of an exemplary method 200 of automatic TGC of an ultrasound image. The data collected by an ultrasound imaging device is shown here as image data 201. Image data 201 preferably includes one or more echogenic data sets 202, where each echogenic data set 202 contains data collected while the ultrasound imaging device is located in a single position or orientation. The data within each echogenic data set 202 preferably represents the amplitude of each received echo and the time each echo was received. An image processing algorithm 204 is preferably applied to echogenic data sets 202 to generate time-gain compensated data sets 206, which can then be used in the generation of time-gain compensated image 208. The image processing algorithm is preferably capable of time-gain compensating each echogenic data set 202 separately based solely on the data values within that particular echogenic data set 202.

Figure 3:
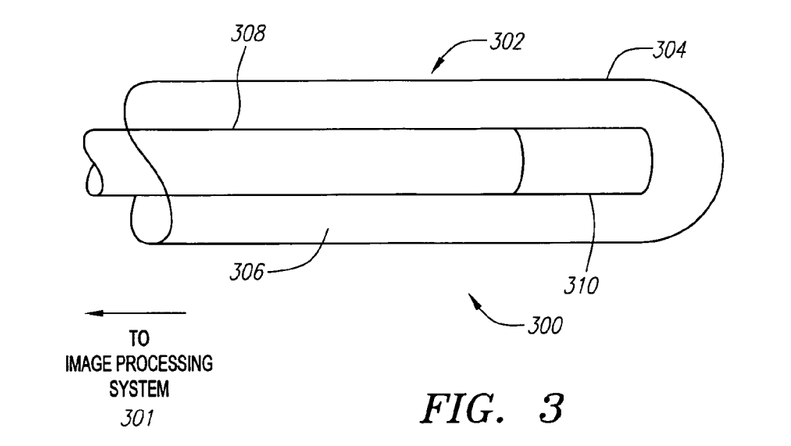
FIG. 3 depicts a cross-sectional view of an exemplary embodiment of an intravascular ultrasound (IVUS) imaging system.

For purposes of illustration, the systems and methods provided herein will be described in the context of exemplary intravascular ultrasound (IVUS) imaging system. However, one of skill in the art will recognize that the systems and methods provided herein are not limited to IVUS imaging and can be used with any ultrasound imaging system. FIG. 3 depicts an exemplary embodiment of IVUS imaging system 300. In this embodiment, IVUS imaging system 300 includes an intravascular device 302 having an elongate tubular member 304 with an inner lumen 306 located therein. Inner lumen 306 is configured to slidably receive a central core 308. Ultrasound imaging device 310 is located on the distal end of central core 308 and is communicatively coupled with image processing system 301 (not shown) via a central core 308. Ultrasound imaging device 310 is configured to image the interior of a blood vessel and output an imaging signal to image processing system 301, which preferably processes the signal and stores it as image data 201. Ultrasound imaging device 310 can be any type of ultrasound imaging device such as a linearly translatable transducer, a rotatable transducer, a multiple transducer array and the like.

Figure 4:
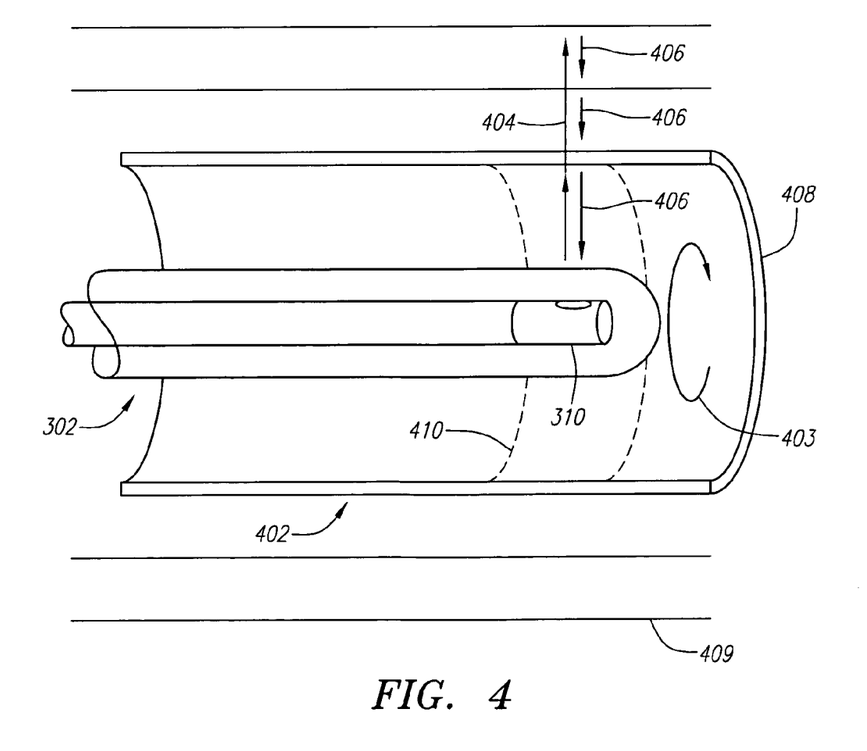
FIG. 4 depicts a cross-sectional view of an exemplary embodiment of ultrasound imaging device within a blood vessel.

FIG. 4 depicts an exemplary embodiment of ultrasound imaging device 310 within a blood vessel 402. In this embodiment, ultrasound imaging device 310 is a rotatable transducer used to image a radial cross-sectional portion 410 of vessel 402. As imaging device 310 rotates in direction 403, an ultrasound pulse, or wave, 404 is transmitted into vessel wall 408 and surrounding tissue 409 and the resulting echoes 406 are received. This process is referred to herein as an imaging cycle, and preferably multiple imaging cycles take place during each rotation with each cycle occurring during a narrow range of movement by imaging device 310.

In one example, imaging device 310 performs an imaging cycle once for every degree of rotation, resulting in 360 transmission/receive cycles in one rotation. It should be noted that one of skill in the art will readily recognize that any desired number of imaging cycles can occur in each rotation, and any number of cycles can occur at each position within the rotation. Imaging device 310 outputs an imaging signal to communicate the receipt of the echoes to image processing system 301, which processes the signal and stores the resulting echo data in echogenic data set 202. As mentioned above, preferably one echogenic data set 202 is created for each imaging cycle and hence each angular position of imaging device 310.

As mentioned above, the systems and methods described herein can be implemented with any type of ultrasound imaging device 310, including a transducer array. The collection of image data 201 with a transducer array 310 is similar to the method of collecting image data 201 with a rotatable transducer 310 as described with regard to FIG. 4. Each transducing element within transducer array 310 outputs an imaging signal to communicate the receipt of echoes to image processing system 301, which processes the signals and stores the resulting echo data in echogenic data sets 202. Preferably, one echogenic data set 202 is created for each transducing element for every imaging cycle and, hence, each location within the imaged region of blood vessel 402.

Figure 5:
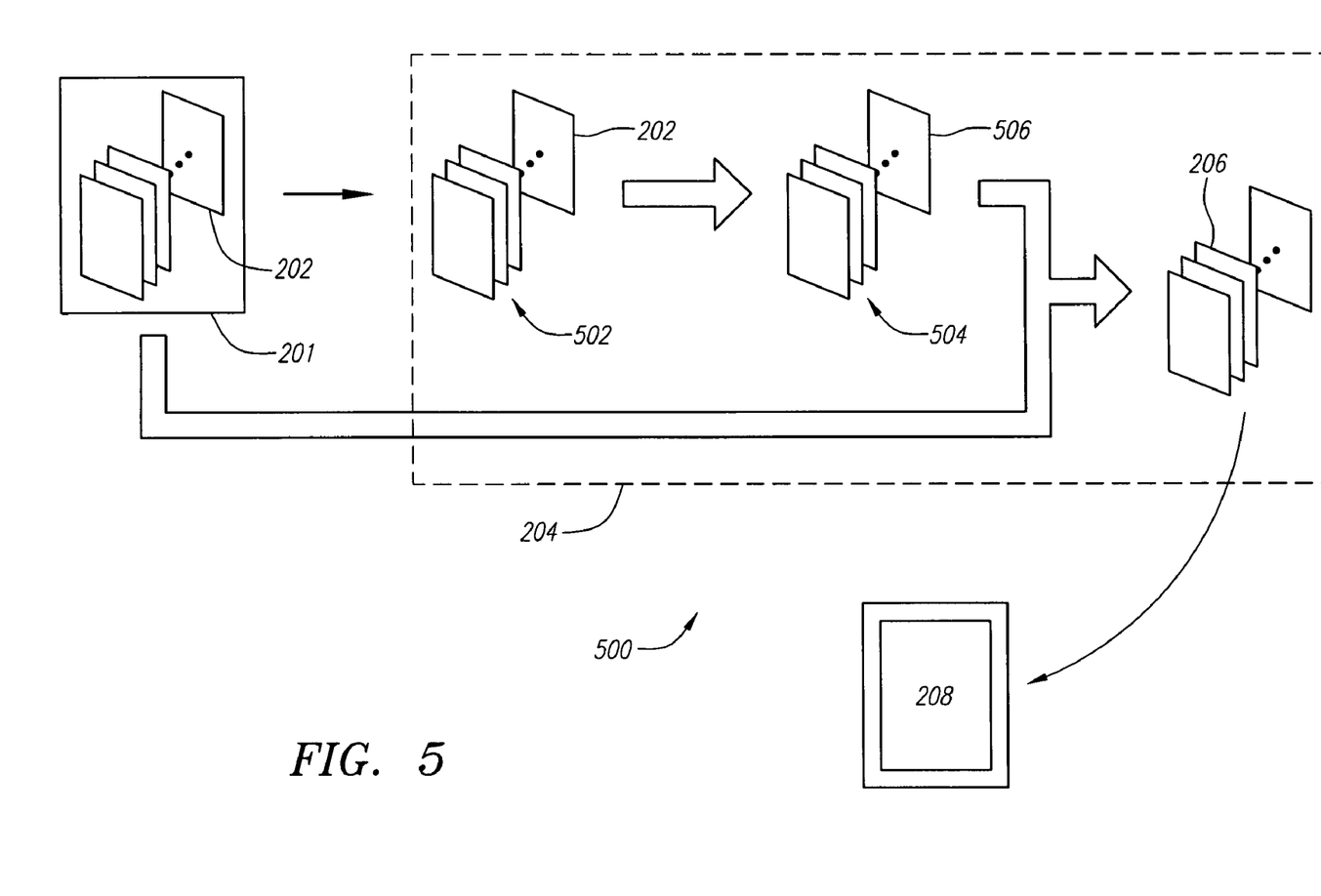
FIG. 5 depicts a block diagram of an exemplary method of automatic TGC with an image processing algorithm.

TGC is then applied to echogenic data sets 202 with image processing algorithm 204. FIG. 5 is a block diagram depicting one example method 500 of TGC with an image processing algorithm 204. First, a desired number of echogenic data sets 202 is selected and designated as echogenic group 502. Any number of data sets 202 can be designated as group 502. Image processing algorithm 204 then generates TGC function group 504 from echogenic group 502. TGC function group 504 is a collection of TGC functions 506, where each function 506 preferably corresponds to one of the echogenic data sets 202 within group 502. Image processing algorithm 204 then applies TGC function group 504 to the echogenic data sets 202 within image data 201 to generate time-gain compensated data sets 206, which can then be used in the generation of time-gain compensated image 208. The time-gain compensation of echogenic data sets 202 preferably occurs in real-time such that there is minimal delay between the collection and visual display of image data 201, although image data 201 can be buffered if necessary to prevent delays.

Preferably, all of the echogenic data sets 202 are placed within group 502 so that each data set 202 will have a single corresponding TGC function 506. If less than all of the echogenic data sets 202 are selected, each TGC function 206 is applied to multiple data sets 202 in order to generate time-gain compensated data sets 506. In this case, the selected echogenic data sets 202 are preferably chosen based upon their corresponding positions within image 508. For instance, in the example where 360 data sets 202 are collected for each rotation of transducer 310, one echogenic data set 202 for every 90 degrees of rotation could be placed within echogenic group 504 for input to image processing algorithm 204. The TGC function 506 generated from each selected echogenic data set 202 is then preferably applied to each of the 90 echogenic data sets 202 within the corresponding 90 degree section. In this manner, the echogenic data sets are time-gain compensated separately based on the position of the echogenic data set 202 within the ultrasound image 508. This is a more precise implementation than conventional TGC techniques which apply a single gain value to each depth across image 508 without regard to location.

Figure 6:
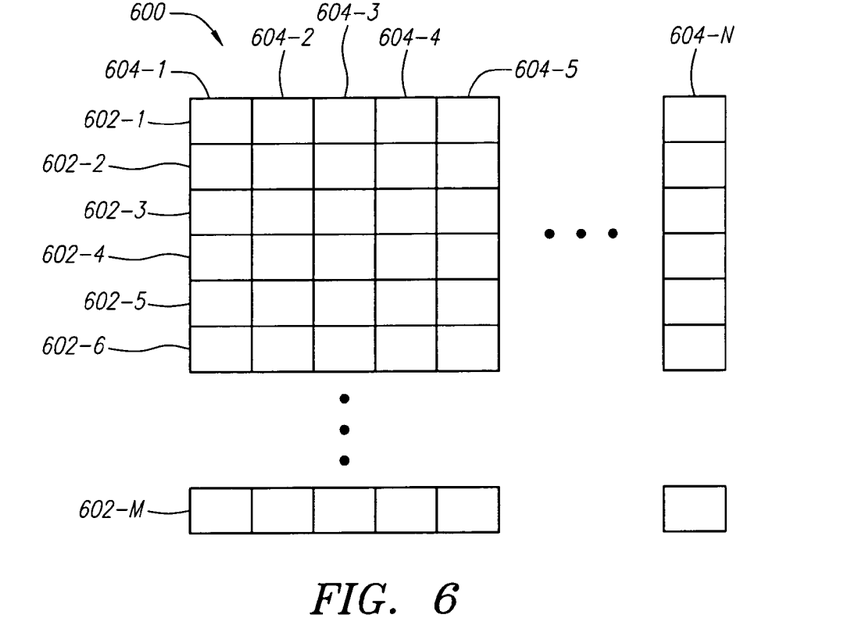
FIG. 6 depicts a block diagram of an exemplary data matrix for use in automatic TGC.
Figure 7:
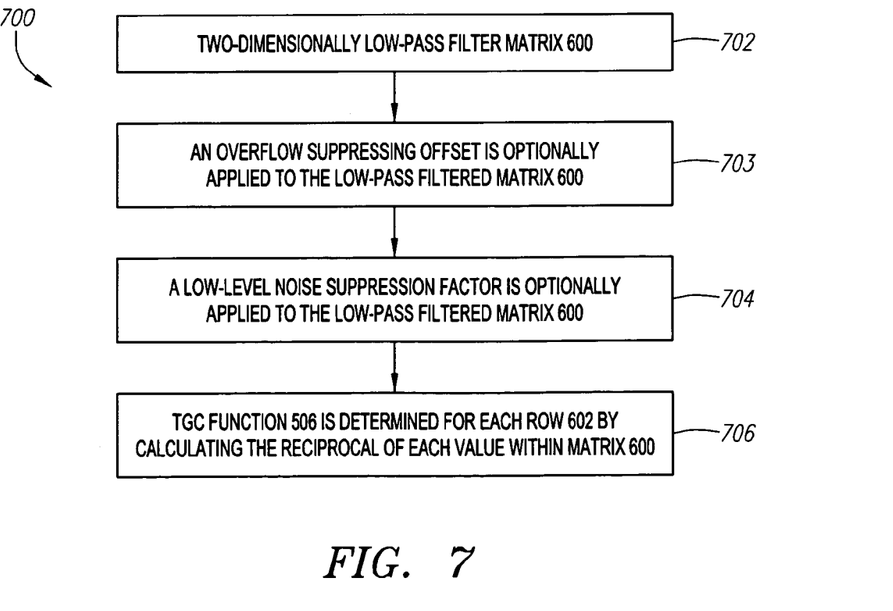
FIG. 7 depicts a flow chart of another exemplary method of automatic TGC with an image processing algorithm.

The following discussion with regard to FIGS. 6-7 describes another example method of automatic TGC using image processing algorithm 204. As stated above, echogenic data sets 202 collected during one rotation can be used to form one ultrasound image 508 of blood vessel 402. Before applying image processing algorithm 204, echogenic data sets 202 within group 502 are combined into a data matrix, such as exemplary data matrix 600 depicted in FIG. 6. Here, data matrix 600 includes M rows 602 and N columns 604. Each row 602 (labeled 602-1 through 602-M) contains one echogenic data set 202 and corresponds to one angular position of imaging device 310. Each column 604 (labeled 604-1 through 604-N) contains data corresponding to the amplitude of a each echo 406 received during the imaging cycle. Each column 604 can also contain data corresponding to the time echo 406 was received, or columns 604 can be distributed within matrix 600 such that each column 604 corresponds to a point in time and the like. The presence of data within that column 604 indicates that an echo 406 was received at that time and the magnitude of the data indicates the strength/amplitude of the received echo 406.

FIG. 7 depicts an example method 700 of automatic TGC using image processing algorithm 204. In this example, group 502 includes each echogenic data set 202 collected during one rotation of transducer 310. At 702, image processing algorithm 204 is used to locally average the data magnitudes within matrix 600. This local averaging reduces any rapid or gross variations along columns 604. In one embodiment, the local averaging is accomplished by two-dimensional low-pass filtering of matrix 600, although one of skill in the art will recognize that any technique which reduces rapid variations in magnitude can be used. At 706, algorithm 204 is used to determine TGC function 506 for each row 602 (i.e., echogenic data set 202). In this embodiment, this includes calculating the reciprocal of each amplitude value within matrix 600.

Image processing algorithm 204 can apply an overflow suppressing offset to the low-pass filtered matrix 600 prior to calculating the reciprocal if necessary. Also, algorithm 204 can apply a low-level noise suppression factor to the low-pass filtered matrix 600 prior to calculating the reciprocal in order to suppress the overamplification of any low-level noise, if necessary. In one example, the low-level noise suppression factor is the low-pass filtered matrix 600 raised to a fractional power, such as 0.25. The optional steps of applying an overflow suppressing offset and low-level noise suppression factor are depicted as 703 and 704, respectively. Finally, at 708, the magnitudes of data sets 202 within original matrix 600 are adjusted. More specifically, TGC function 506, which, in this embodiment, is the reciprocal matrix, is applied to the echogenic data sets 202 forming original matrix 600 to generate time-gain compensated data sets 506. One of skill in the art will readily recognize that the use of reciprocal values as TGC function 506 is only one example of the many different magnitude adjustment functions that can be used.

In this embodiment, each of the time-gain compensated data sets 506 is compensated based solely on the data within that data set 202. This is an optimal and highly granular approach which minimizes the risk that data sets 202 will be improperly time-gain compensated, as in conventional techniques where a single gain value is derived for each depth and applied across the entire image. Also, the systems and methods provided herein determine the appropriate TGC regardless of the depth at which the echo was generated or the time it was received. This is in contrast with conventional techniques that determine gain compensation values for a select number of pre-determined depths and then interpolate the gain values to be applied to the image at any intervening depths. Furthermore, the time-varying amplification applied to echogenic data sets 202 by TGC functions 206 can be the sole time-varying amplification applied for the purposes of TGC and can fully compensate the ultrasound image without the need for predetermined TGC baselines to be applied first.

One of skill in the art will readily recognize that numerous image processing algorithms 204 can be used to time-gain compensate matrix 600. Any method or algorithm capable of computing the TGC for an ultrasound image can be used. Furthermore, the systems and methods for TGC described herein can be applied to each ultrasound image, or can be applied only to selected frames. For instance, TGC functions 206 can be determined for one image and then applied to a desired number of successive images until new time-gain functions are determined.

In the foregoing specification, the invention has been described with reference to specific embodiments thereof. It will, however, be evident that various modifications and changes may be made thereto without departing from the broader spirit and scope of the invention. For example, each feature of one embodiment can be mixed and matched with other features shown in other embodiments. Features and processes known to those of ordinary skill may similarly be incorporated as desired. Additionally and obviously, features may be added or subtracted as desired. Accordingly, the invention is not to be restricted except in light of the attached claims and their equivalents.

What is claimed is:

1. A method of automatic time-gain compensation (TGC) with an image processing algorithm, comprising:

receiving ultrasound image data comprising a plurality of echogenic data sets, wherein the ultrasound image data is representative of echoes received by an intravascular imaging device configured for operation within a body lumen, the ultrasound image data corresponds to a radial cross-section of the body lumen, and each echogenic data set corresponds to a separate angular location within the radial cross-section of the body lumen;

determining a plurality of TGC functions for the plurality of echogenic data sets, wherein each TGC function is determined from a separate echogenic data set; and automatically applying the TGC functions to the plurality of echogenic data sets.

2. The method of claim 1, wherein determining the plurality of TGC functions comprises locally averaging the echogenic data sets.

3. The method of claim 2, wherein locally averaging comprises low pass filtering the echogenic data sets.

4. A method of automatic time-gain compensation (TGC) with an image processing algorithm, comprising:

receiving ultrasound image data comprising a plurality of echogenic data sets, wherein the ultrasound image data is representative of echoes received by an intravascular imaging device configured for operation within a body lumen, the ultrasound image data corresponds to a radial cross-section of the body lumen, and each echogenic data set corresponds to a separate angular location within the radial cross-section of the body lumen;

determining a plurality of TGC functions for the plurality of echogenic data sets, wherein each TGC function is determined from a separate echogenic data set, and wherein determining the plurality of TGC function comprises:
locally averaging the echogenic data sets; and
determining the reciprocal of each locally averaged echogenic data set; and automatically applying the TGC functions to the plurality of echogenic data sets.

5. The method of claim 4, wherein determining the plurality of TGC functions comprises applying a noise suppression factor to the echogenic data set.

6. The method of claim 5, wherein applying the TGC functions comprises multiplying the original echogenic data sets by the reciprocal data sets.

7. The method of claim 1, wherein a TGC function is determined for each echogenic data set in the image data.

8. The method of claim 1, wherein the determined TGC function is the sole time-varying amplification applied to time-gain compensate the image data.

9. The method of claim 1, wherein the image data includes image data of the interior of a body lumen.

10. The method of claim 9, wherein each echogenic data set is representative of echoes received during one imaging cycle.

11. The method of claim 10, wherein each imaging cycle occurs at a separate angular location within a radial cross-section of the body lumen.

12. The method of claim 1, further comprising automatically applying the TGC functions to the plurality of echogenic data sets without user intervention.

13. An ultrasound image processing system configured for automatic time-gain compensation (TGC) with an image processing algorithm, comprising:

an image processing system configured to process an imaging signal generated by an intravascular ultrasound imaging device into a plurality of echogenic data sets, wherein each echogenic data set corresponds to a separate angular location within a radial cross-section of a body lumen;

the image processing system adapted to determine a plurality of TGC functions for the plurality of echogenic data sets, wherein each TGC function is determined from a separate echogenic data set, and adapted to apply the TGC functions to the plurality of echogenic data sets automatically.

14. The system of claim 13, wherein the image processing system is further configured to locally average the echogenic data sets.

15. The system of claim 14, wherein the image processing system is further configured to locally average the echogenic data sets by low pass filtering the echogenic data sets.

16. An ultrasound image processing system configured for automatic time-gain compensation (TGC) with an image processing algorithm, comprising:

an image processing system configured to process an imaging signal generated by an intravascular ultrasound imaging device into a plurality of echogenic data sets, wherein each echogenic data set corresponds to a separate angular location within a radial cross-section of a body lumen;

the image processing system adapted to determine a plurality of TGC functions for the plurality of echogenic data sets, wherein each TGC function is determined from a separate echogenic data set, and adapted to apply the TGC functions to the plurality of echogenic data sets automatically;

wherein the image processing system is further configured to locally average the echogenic data sets by low pass filtering the echogenic data sets, and determine the reciprocal of the locally averaged data sets.

17. The system of claim 16, wherein the image processing system is further configured to apply an overflow suppressing offset to the locally averaged data sets prior to determining the reciprocal.

18. The system of claim 16, wherein the image processing system is further configured to apply a noise suppression factor to the locally averaged data sets prior to determining the reciprocal.

19. The system of claim 16, wherein the image processing system is further configured to multiply the reciprocal data sets by the original echogenic data sets.

20. The system of claim 13, wherein the image processing system is configured to determine a TGC function for each echogenic data set in the image data.

21. The system of claim 13, wherein the determined TGC function is the sole time-varying amplification applied to the image data for TGC.

22. The system of claim 13, wherein each echogenic data set is representative of echoes received during one imaging cycle.

23. The system of claim 22, wherein the ultrasound imaging device is configured to perform each imaging cycle at separate angular locations within a radial cross-section of the body lumen.

24. The system of claim 13, wherein the image processing system is further adapted to apply the TGC functions to the plurality of echogenic data sets automatically-without user intervention.

* * * * *